United States Patent [19]
Gerber

[11] 3,938,510
[45] Feb. 17, 1976

[54] FINGER SPLINT WITH TRACTION MEANS
[76] Inventor: Edward M. Gerber, 12 Carriage Drive, Lexington, Mass. 02173
[22] Filed: Aug. 5, 1974
[21] Appl. No.: 494,525

[52] U.S. Cl. .............................. 128/85; 128/87 A
[51] Int. Cl.² ........................................ A61F 5/04
[58] Field of Search .......... 128/85, 87 A, 77, 84, 83

[56] References Cited
UNITED STATES PATENTS
2,646,794  7/1953  Baer ...................................... 128/85

FOREIGN PATENTS OR APPLICATIONS
589,990  6/1925  France .............................. 128/87 A

OTHER PUBLICATIONS

"Hart Finger Splint," Zimmer Fracture Appliances Catalogue, Aug. 1947, p. 93.

Primary Examiner—Richard A. Gaudet
Assistant Examiner—J. Yasko
Attorney, Agent, or Firm—Wolf, Greenfield & Sacks

[57] ABSTRACT

A finger splint includes means for applying and maintaining a light, positive traction to the end of the splinted finger.

11 Claims, 7 Drawing Figures

FINGER SPLINT WITH TRACTION MEANS

BACKGROUND OF THE INVENTION

My invention relates to an improved splint and, particularly, to an improved finger splint having means for applying a light traction to the splinted finger. The application of traction, i.e., a generally longitudinal tensioning force, to a broken limb or bone has been a long employed medical procedure in the treatment and healing of fractures. Generally, traction promotes proper healing and setting of the bone and also usually tends to alleviate pain resulting from the injury. Typically, the various types of traction devices in use are awkward and bulky mechanical contrivances. While they are suited for use by a relatively immobile bed-ridden patient, e.g. with a broken leg, their general bulky and awkward construction has not lent itself to use in applying traction to fingers or the like which are, of course, comparatively small and usually would not affect the patient's mobility. While smaller traction devices have been proposed in the prior art for applying traction to a splinted finger, they too have been relatively bulky and somewhat more complicated than is desirable. These devices have found little favor with the medical profession and, as a result, a broken finger usually is simply splinted without applying traction to the finger. This, of course, adds to the patient's discomfort. It is among the primary objects of the invention to provide an improved finger splint having means for applying a light traction to the splinted finger which avoids the foregoing and other difficulties in the prior proposed devices.

SUMMARY OF THE INVENTION

The invention includes an elongate splint having a pair of pressure sensitive strips of tape connected to one end of the splint. The splint is placed along the underside of the patient's finger and its rear end extends longitudinally across his palm where it may be secured by tape. The tape strips at the end of the splint are adapted to extend rearwardly from the outer end of the splint so that they may be attached to the sides of the finger, forwardly of the location of the fracture. The tape strips are connected to the outer end of the splint by movable means which enables the tape strips to be drawn forwardly under light tension after the splint has been secured to the hand thus applying a light traction to the end of the broken finger. Means also are provided for maintaining the desired amount of forward tension on the end of the finger by securing the tape strips in their tensioned position.

A general object of the invention is to provide an improved finger splint which includes means for applying a light traction force to the end of the splinted finger.

Another object of the invention is to provide a traction finger splint which is compact and is no more bulky, in use, than a conventional splint having no traction means.

A further object of the invention is to provide an improved finger splint having traction means which is inexpensive and simple to use.

Still another object of the invention is to provide a finger splint of the type described which also provides additional protection to the end of the patient's finger.

DESCRIPTION OF THE DRAWINGS

The foregoing and other objects and advantages of the invention will be understood more fully from the following further description thereof, with reference to the accompanying drawings wherein.

DESCRIPTION OF THE PREFERRED EMBODIMENT

Figure 1:
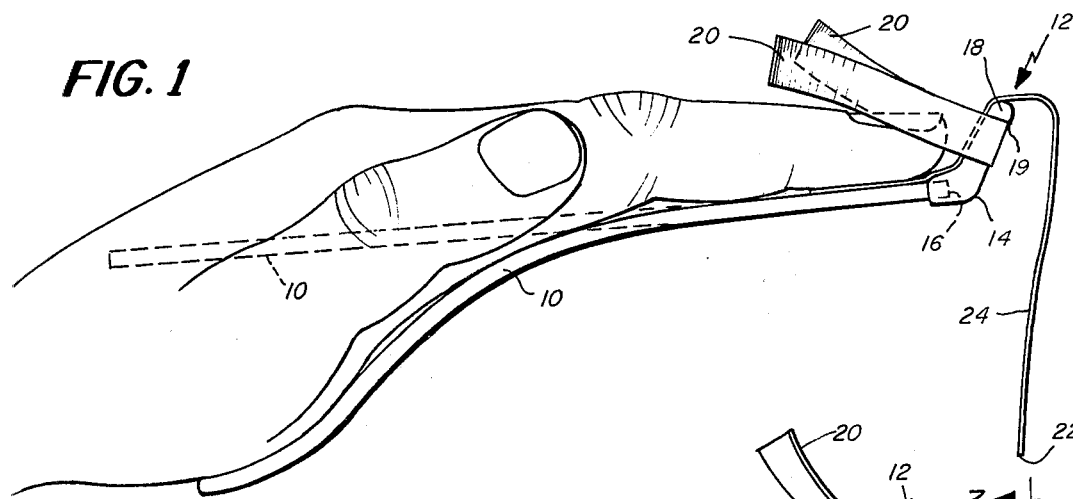
FIG. 1 is a side elevation of the splint in proper orientation with regard to the patient's finger and hand and before the splint or the traction means is attached to the finger and hand.
Figure 2:
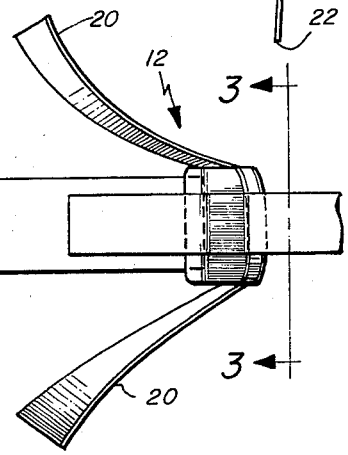
FIG. 2 is a plan view of the improved splint.
Figure 3:
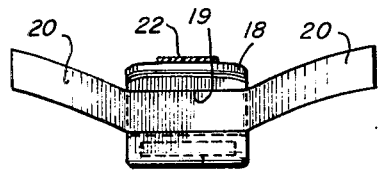
FIG. 3 is an end view of the splint as seen along the line 3—3 of FIG. 2.

As shown in FIGS. 1-3, the invention includes an elongate splint 10 having forward and rearward ends which is generally flat and is adapted to underlie the injured finger and extend across the user's palm as shown. The splint 10 preferably is made from a light deformable metal such as aluminum, or a deformable plastic so that it may be easily bent from its initially straight configuration, shown in phantom in FIG. 1, to a desired configuration which will fit comfortably against the patient's finger and palm as suggested in FIGS. 1 and 4. It may be noted that while a deformable type of splint generally is preferred, the invention may also be employed in connection with a more rigid type of splint, e.g., one made from wood.

Figure 4:
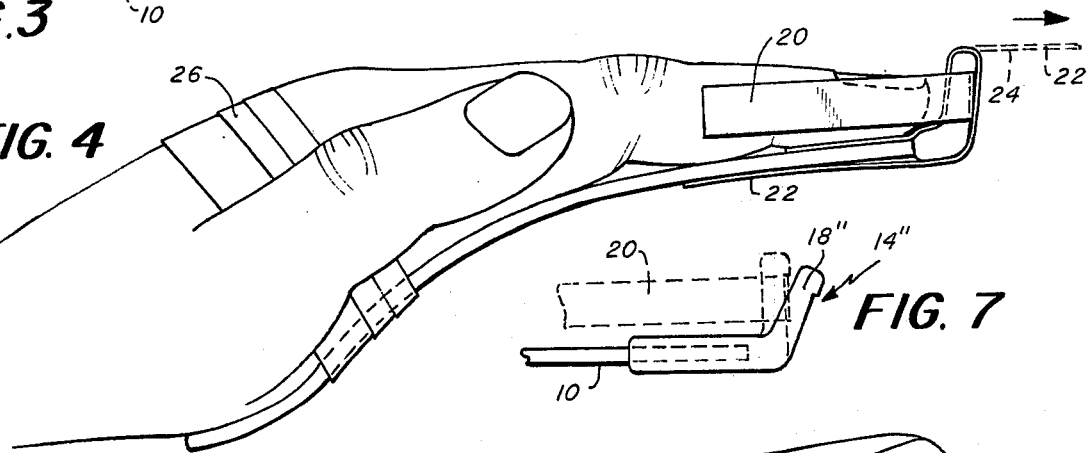
FIG. 4 is a side elevation similar to FIG. 1 illustrating the manner in which the splint and traction means are attached.
Figure 5:
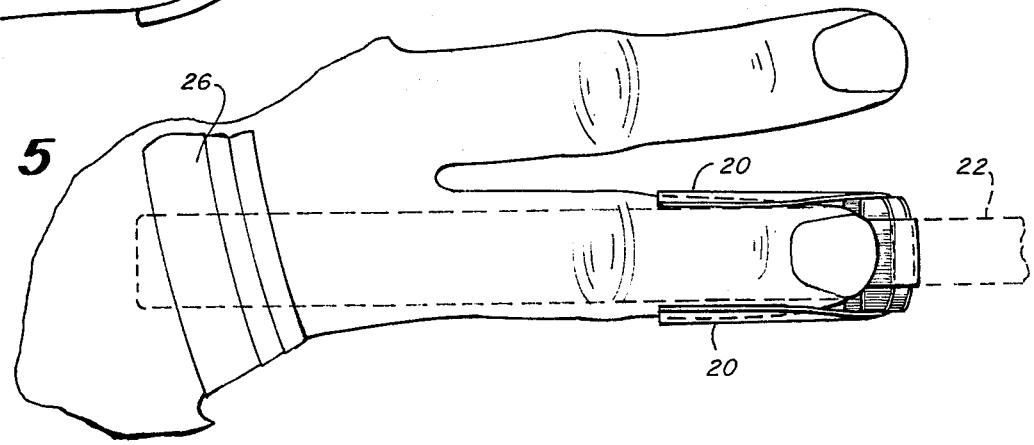
FIG. 5 is a plan view of the splinted finger and hand of FIG. 4.

A traction device, indicated generally by the reference character 12 is mounted to the forward outer end of the splint. In the illustrative embodiment of the invention, the traction device 12 is shown as including a generally L-shaped flexible member 14 which is secured to the outer end of the splint 10 by any suitable means. For example, the member 14 may be formed from a single piece of suitable flexible rubber or plastic having a first portion which may be molded directly onto the end of the splint 10. Alternatively, the member 14 may be molded separately and may be provided with a socket 16 in the first portion formed therein to receive the end of the splint 10 in secure engagement therewith. The member 14 includes a generally upwardly extending end portion 18 which may be flexed in a generally pivotal manner toward or away from the tip of the finger about the juncture region of the first and end portions as suggested in FIGS. 1 and 4. The upwardly extending end portion 18 of the member 14 preferably has a substantial width so that it may generally cover the tip of the finger to protect it. A pair of adhesive tape strips 20 are firmly attached to the end portion 18 of the flexible member 14 so that they may extend rearwardly and along opposite sides of the injured finger as shown in FIGS. 4 and 5. In some instances it may be desirable to provide a third adhesive tape strip to underlie and be secured to the undersurface of the patient's finger, the third tape strip also being connected to the flexible member 14. The upper end of end portion 18 may be provided with a shoulder 19 if desired to help retain the tape strips 20 in position. The inwardly facing surfaces of the tape strips 20 are provided with a pressure sensitive adhesive and a variety of such pressure sensitive tape materials are commercially available. The tape strips 20 may be defined by a single strip which is wrapped about and secured to the end portion 18 of the member 14 as shown. It should be noted that the side tape strips 20 may be attached to the member 14 by other means. Whatever means employed, however, the tape strip 20 should be movable slightly and generally longitudinally of the splint 10 in unison with movement of the upstanding end portion 18. The tape strips 20 preferably are fabricated from a relatively nonstretchable type of adhesive tape. In this embodiment of the invention, a tensioning tape strip 22 also is connected to the flexible upstanding portion 18 of member 14 and has a pressure sensitive adhesive coating on its inner surface 24 to enable the tape strip 22 to be wrapped underneath the splint 10 and be secured thereto as suggested in FIG. 4. The securing tape strip 22 may have a portion attached to the upper surface of the splint and the finger-facing surface of the member 14, and having a free end which can be wrapped about the outwardly facing surface of the member 14 and the underside of the splint 10. It should be understood, however, that the securing tape strip 22 may be connected to the member 14 by other means in a manner which will enable the device to operate in its intended manner.

In use, the splint 10 is bent from its straight configuration to one which conforms comfortably to the underside of the user's finger and palm. The rearward end of the splint 10 is then taped securely to the patient's hand by adhesive tape 26. The side tape strips 20 then are taped to the sides of the patient's finger forwardly of the location 28 of the fracture. With the side tape strips 20 secured to the end of the finger, the tensioning strip 22 is pulled slightly outwardly away from the finger as suggested by the arrow in FIG. 4 to apply a slight but sufficient traction to the finger. The tape strip 22 then is drawn downwardly and is wrapped about the underside of the splint and is firmly attached thereto by the pressure sensitive adhesive 24 as shown in solid in FIG. 4. It may be noted that before securing the side tape strips 20 to the sides of the finger, the end portion 18 of the member 14 may be flexed slightly inwardly toward the tip of the finger as suggested in FIG. 4 and by comparison with FIG. 1. By preliminarily flexing the tip 18 so that it extends generally perpendicularly from the splint, it is insured that the subsequent tensioning of the tape strips 20 will be applied to the end of the finger along a direction which is substantially longitudinal of the end of the finger.

From the foregoing it may be seen that the device and technique which it employs greatly simplify the application of traction to an injured finger. The invention avoids the use of awkward or somewhat complex mechanical devices which have retarded the use of traction in the treatment of injured fingers.

Various configurations may be employed for the member 14, the drawings showing but one such configuration. Other means may be employed for connecting the tape strips 20 to the member 14 to enable the tape strips 20 to be drawn forwardly with the member 14 to apply traction. For example, the tape strips 20 could be embedded directly in the end portion 18 during the molding procedure.

Figure 6:
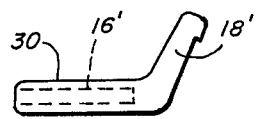
FIG. 6 is a side elevation of a modified embodiment of the invention.

The invention may also be incorporated in the form of an attachment to a conventional splint. As shown in FIG. 6, the tip attachment may be fabricated from a single piece of molded rubber or plastic having a connective portion 30 and a deep longitudinal socket 16' formed therein to receive firmly the outer end of the splint 10. The connective portion 30 preferably is elongated to enhance its firm connection to the end of the splint when it is slipped over the end of the splint. The flexible member 18' is integral with and extends, at an angle, from the connective portion so that when secured to the splint the wall portion 18' will extend generally upwardly. The side tape strips 20 and securing tape strips 22 then may be attached in the same manner as described above.

It may be noted that the simplicity of the device also enables the patient to adjust the degree of traction himself with ease simply by stripping the tape 22 from the bottom of the splint, retensioning the tape 22 and then reattaching it to the underside of the splint 10.

Figure 7:
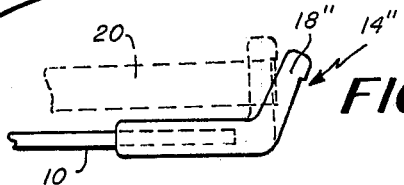
FIG. 7 is a side elevation of a further embodiment of the invention.

FIG. 7 shows a further embodiment of the invention in which the tensioning strip may be omitted, if desired. In this embodiment, the flexible tip 14" is also of a sufficient resilience such that the wall portion 18" will be biased firmly towards its relaxed position shown in solid. With this embodiment securely attached to the end of the splint 10 and with the splint taped securely to the patient's palm, the flexible, resilient end portion 18" is flexed toward the tip of the finger as shown in phantom. The side tape strips 20 then are attached to the sides of the finger while maintaining the resilient end portion 18" in its flexed configuration. When the finger has been taped as described, the inherent resilience of the end portion 18", will itself apply a light traction force to the end of the finger.

It should be understood that the foregoing description of the invention is intended merely to be illustrative thereof and that other embodiments and modifications may be apparent to those skilled in the art without departing from its spirit or from the scope of the appended claims.

Having thus described the invention what I desire to claim and secure by Letters Patent is:

1. An article for use in the treatment of an injured finger or the like comprising:

an elongate splint having an outer forwardly extending end;

an attachment member having a first portion attached to the outer end of the splint, said member including an upwardly extending end portion extending from said first portion of said attachment member, said member being flexible to enable said end portion to be flexed with respect to said first portion of the member and splint in a direction which is forwardly and away from the end of said finger;

finger attaching means connected to the upwardly extending end portion of said member and adapted to extend generally rearwardly therefrom for attachment to said finger; and means for urging the upwardly extending end of the member in a generally forward direction and away from the end of the finger to a tensioned position.

2. A device as defined in claim 1 wherein said means for urging the upwardly extending end of said member in said forward tensioned position comprises:

said end portion of said member being of resilient construction and having a relaxed configuration in which said end portion is disposed in a predetermined position, the end portion of the member being further flexible rearwardly of said predetermined position;

whereby when said finger attaching means is attached to said finger while said end portion is urged rearwardly from its relaxed configuration, said resilience of said end portion of said member will impart said longitudinal tensioning to said finger.

3. An article as defined in claim 1 further comprising: the width of said end portion being approximately equal to the width of said finger.

4. An article for use in the treatment of an injured finger or the like comprising:
- an elongate splint having an outer forwardly extending end;
- an attachment member having a first portion attached to the outer end of said splint, said member including an upwardly extending end portion and being constructed and arranged as to be flexible to enable said end portion to be urged at least away from the end of said finger;
- adhesive tape finger attaching means connected to the end of said flexible end portion of said member and adapted to extend generally rearwardly therefrom for attachment to a finger associated with said splint;
- said member being constructed and arranged as to be movable at least away from said finger and in a direction which is generally longitudinal of said splint to tension said finger attaching means generally forwardly; and
- means for maintaining said member in said forwardly tensioned position, said tensioning means including a tape strip connected to said end portion of said member to enable said member to be urged away from said finger to a forwardly tensioned position and to be wrapped about said member and adhesively attached to the underside of said splint to secure said member in said forwardly tensioned position.

5. An attachment for a finger splint or the like comprising:
- a molded one piece member having a connective portion and an end portion extending at an angle from said connective portion, said connective portion having a socket formed longitudinally therein to receive the end of a finger splint and be secured to said finger splint;
- said end member extending from said connective portion and being flexible with respect to said connective portion.

6. An attachment as defined in claim 5 further comprising:
- means defining an undercut shoulder at the forwardly facing surface of the end portion of the member, adjacent the outer end of the end portion.

7. An attachment as defined in claim 5 further comprising:
- the member being constructed so that its end portion also is resilient with respect to said connective portion.

8. An improved finger splint comprising:
- an elongate finger splint;
- a molded, one piece member having a connective portion attached to one end of the splint and an end portion extending from the connective portion at an angle to the connective portion, the end portion being flexible with respect to the connective portion to enable the end portion to be pivoted with respect to the connective portion at the juncture region between the end and connective portions.

9. An article as defined in claim 8 wherein the connective and end portions of the member define a generally L-shaped configuration.

10. An article as defined in claim 9 wherein the end portion is flexible in both forward and rearward directions.

11. An article as defined in claim 10 wherein the member is fabricated from a resilient material.

* * * * *